United States Patent
Deshpande et al.

(10) Patent No.: US 6,833,459 B2
(45) Date of Patent: Dec. 21, 2004

(54) PROCESS FOR THE PREPARATION OF THIAZOLE INTERMEDIATE

(75) Inventors: Pandurang Balwant Deshpande, Chennai (IN); Parven Kumar Luthra, Chennai (IN); Rajesh Vyas, Chennai (IN); Ramakrishna Kamma, Chennai (IN)

(73) Assignee: Orchid Chemicals & Pharmaceuticals Limited, Chennai (IN)

(*) Notice: Subject to any disclaimer, the term of this patent is extended or adjusted under 35 U.S.C. 154(b) by 0 days.

(21) Appl. No.: 10/309,812

(22) Filed: Dec. 5, 2002

(65) Prior Publication Data

US 2003/0204095 A1 Oct. 30, 2003

(30) Foreign Application Priority Data

Apr. 26, 2002 (IN) .................... 325/MAS/2002

(51) Int. Cl.$^7$ ............................................. C07D 277/24
(52) U.S. Cl. ........................................ 548/200
(58) Field of Search ........................ 548/200

(56) References Cited

FOREIGN PATENT DOCUMENTS

| EP | 0 343 640 B1 | 10/1994 |
|---|---|---|
| JP | 45-36908 | 11/1970 |

OTHER PUBLICATIONS

Sinha et al, 2002, CAS:137:234008.*

* cited by examiner

*Primary Examiner*—Rita Desai
*Assistant Examiner*—Robert Shiao
(74) *Attorney, Agent, or Firm*—Oliff & Berridge, PLC

(57) ABSTRACT

The present invention provides a process for the preparation of 4-methyl-5-formyl-thiazole of the formula (I)

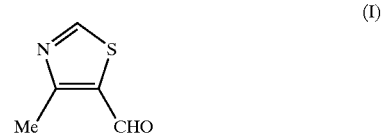

which comprises reducing the thiazole ester of the formula (III) to thiazole alcohol of the formula (IV), using sodium borohydride in the presence of AlCl$_3$ in a solvent and oxidising using an oxidizing agent the thiazole alcohol of the formula (IV) to obtain 4-methyl-5-formyl-thiazole of the formula (I).

12 Claims, No Drawings

PROCESS FOR THE PREPARATION OF THIAZOLE INTERMEDIATE

FIELD OF THE INVENTION

The present invention provides a process for the preparation of thiazole derivative. More particularly, the present invention relates to a process for the preparation of 4-methyl-5-formyl-thiazole of the formula (I).

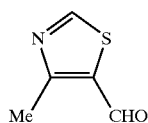
(I)

4-Methyl-5-formyl-thiazole of the formula (I) is a useful key intermediate in the preparation of Cefditoren pivoxil of the formula (II), which is a well known antibiotic.

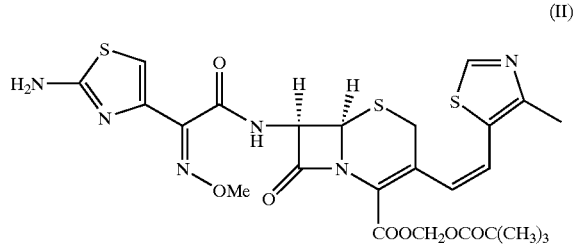
(II)

BACKGROUND OF THE INVENTION

Harrington et al (J. Chem. Soc., (1939) 443–446) described a process for the preparation of 4-methyl-5-formyl-thiazole of the formula (I), starting from ethyl 4-methylthiazole-5-carboxylate which was converted through the amide to the nitrile, which in turn was converted to the aldehyde. The process involves the preparation of the nitrile compound by using $POCl_3$, which is highly corrosive, hazardous and difficult to handle in large scales.

Yokoyama et al (Stud. Surf. Sci. Catal., (1994), 90, 47–58) reports a process for the direct hydrogenation of aromatic carboxylic acid to the corresponding aldehydes. The catalyst used is modified zirconia.

EP patent number 0 343 640 claims a process for the preparation of heterocyclic aldehyde from the corresponding carboxylic acid and its derivatives using a catalyst consisting of an oxide of Zinc, Yitrium, lanthanides or Group 4A elements. The oxides of these metals are prepared at very high temperature such as 200 to 900° C. Methyl 4-methylthiazole-5-carboxylate was hydrogenated using an oxide catalyst composed of chromium, zirconium to produce 4-methylthiazole-5-carboxaldehyde also at very high temperature ranging from 200 to 700° C., which makes the process industrially non-workable.

JP 45036908 discloses a process for the preparation of 4-methyl-5-hydroxymethyl thiazoles from 4-methyl-5-(ethoxycarbonyl) thiazoles using $LiAlH_4$ and diethylether. The process suffers the following disadvantages: The reducing agent, $LiAlH_4$ cannot be handled in the large operations as it is an hazardous reagent. This problem has been overcome by the use of sodium borohydride, in the presence of $AlCl_3$ in the present invention as the rate of evolution of hydrogen in the process is controllable and hence, the reaction as a whole is easy to handle.

To overcome the problems associated in the preparation of 4-methyl-5-formyl-thiazole of the formula (I), we focussed our research to develop a process, which uses non-hazardous materials, industrially workable at ambient temperature and safe to use.

OBJECTIVE OF THE INVENTION

The main objective of the present invention is to provide a process for the preparation of 4-methyl-5-formyl-thiazole of the formula (I), which is useful as an intermediate in the preparation of Cefditoren.

Another objective of the present invention is to provide a process for the preparation of 4-methyl-5-formyl-thiazole of the formula (I), which is commercially viable, high yielding, and with high purity of the product.

SUMMARY OF THE INVENTION

The present invention relates to a process for the preparation of 4-methyl-5-formyl-thiazole of the formula (I)

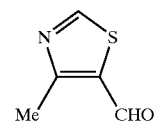
(I)

which comprises oxidising the 4-methyl-5-hydroxymethyl thiazole of the formula (IV) to 4-methyl-5-formyl-thiazole of the formula (I), using an oxidizing agent at a temperature in the range of –10° C. to 50° C., in the presence of a solvent.

In another embodiment of the present invention, there is a provided a process for the preparation of 4-methyl-5-hydroxymethyl thiazole of the formula (IV), which comprises reducing the thiazole ester of the formula (III), wherein R represents ($C_1$–$C_4$) alkyl group such as methyl, ethyl, n-propyl, iso-propyl, tert-butyl to 4-methyl-5-hydroxymethyl thiazole of the formula (IV), using sodium borohydride in the presence of $AlCl_3$ and a solvent, at a temperature in the range of –20° C. to 90° C.

The reaction scheme described above is as shown below.

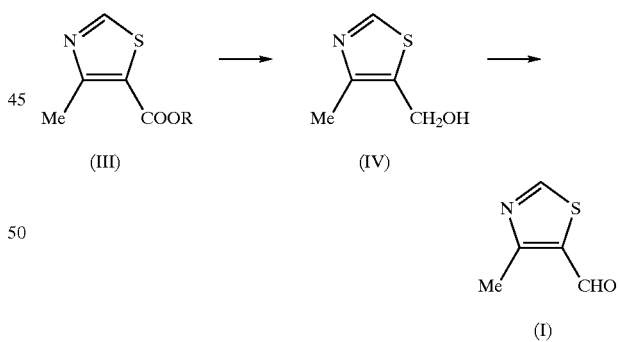

DETAILED DESCRIPTION OF THE INVENTION

In another embodiment of the present invention, the oxidizing agent is selected from pyridinium chlorochromate (PCC), NaOCl and KBr in presence of TEMPO (2,2,6,6-tetramethyl-1-piperidinyloxy free radical) or Jones reagent ($CrO_3$/$H_2SO_4$) in the presence of a solvent selected from dichloromethane or ethylacetate.

In still another embodiment of the present invention, the oxidizing agent is preferably selected from pyridinium chlorochromate or NaOCl and KBr in presence of TEMPO.

In another embodiment of the present invention, reduction is carried out in a solvent selected from ethylene glycol dimethyl ether (monoglyme), THF or diethylene glycol dimethyl ether (diglyme).

The present invention is exemplified by the following examples, which are provided for illustration only and should not be construed to limit the scope of the invention.

EXAMPLE 1

Preparation of 4-methyl-5-hydroxymethyl-thiazole (IV)

Monoglyme (200 ml) was charged and cooled to −10° C. To this NaBH$_4$ (44.0 g) was charged in one lot at −10° C. and stirred for 15 minutes. AlCl$_3$ (50.0 g) was slowly added for 1 hour at −10 to +5° C., stirred for 30 min at 0° C. Then 4-methyl-thiazole-5-carboxylic acid ethyl ester (III) (100.0 g) was added for 1 hour at 0–15° C. The reaction mixture was stirred at 15–25° C. for 4 hours and the progress of reaction was monitored by HPLC. The reaction mixture was poured into mixture of ice (500 g) and conc. HCl (200 ml) and stirred for 30 minutes. The reaction mixture was concentrated at 50–60° C. to remove organic solvents from it and cooled the reaction mixture to 5° C. The pH of the reaction mixture was adjusted with sodium hydroxide solution at 5–15° C. up to 12.5 and heated to 45° C. The reaction mixture was extracted with THF (4×250 ml). Combined THF layers were collected and treated with charcoal at 45° C. THF layer was distilled of at 50° C. to yield the title compound (55–60 g), (purity by HPLC: 97–98%).

EXAMPLE 2

Preparation of 4-methyl-5-hydroxymethyl-thiazole (IV)

Monoglyme (200 ml) was charged and cooled to −10° C. To this NaBH$_4$ (40.0 g) was charged in one lot at −10° C. and stirred for 15 minutes. AlCl$_3$ (47.0 g) was slowly added for 1 hour at −10 to +5° C., stirred for 30 min at 0° C. Then 4-methyl-thiazole-5-carboxylic acid methyl ester (III) (100.0 g) was added for 1 hour at 0–15° C. The reaction mixture was stirred at 15–25° C. for 4 hours and the progress of reaction was monitored by HPLC. The reaction mixture was poured into mixture of ice (500 g) and conc. HCl (200 ml) and stirred for 30 minutes. The reaction mixture was concentrated at 50–60° C. to remove organic solvents from it and cooled the reaction mixture to 5° C. The pH of the reaction mixture was adjusted with sodium hydroxide solution at 5–15° C. up to 12.5 and heated to 45° C. The reaction mixture was extracted with THF (4×250 ml). Combined THF layers were collected and treated with charcoal at 45° C. THF layer was distilled of at 50° C. to yield the title compound (55–60 g), (purity by HPLC: 97–98%).

EXAMPLE 3

Preparation of 4-methyl-5-formyl-thiazole (I)

4-Methyl-5-hydroxymethyl-thiazole (50 gm (0.38 mole)) was added to dichloromethane (300 ml) and stirred for 5 minutes. To this solution, sodium bicarbonate solution (17 g in 250 ml of water) was added at 30–32° C. and stirred the solution for 5–10 minutes at 30–32° C. The reaction mass was cooled to 0° C. and KBr solution (6 g in 10 ml of water) and TEMPO (0.285 g, 0.0018 mole) was added in single lot. To this sodium hypochlorite solution (450 ml of 12.5% w/v) was added in 1 hour at 0–2° C. temperature. The reaction mass was stirred at 0–2° C. and the progress of reaction was monitored by HPLC.

After completion of reaction, the organic layer was separated. The aqueous layer was extracted with dichloromethane (2×125 ml). Dichloromethane layer was collected and washed with alkaline solution (80 ml) followed by brine (125 ml). The dichloromethane layer was dried over Na$_2$SO$_4$ and filtered. The dichloromethane layer was evaporated under reduced pressure to get 4-methyl-5-formyl-1,3-thiazole (36–38 g), (purity by HPLC: 97–98%).

EXAMPLE 4

Preparation of 4-methyl-5-formyl-thiazole (I)

PCC (102 g) was charged to dichloromethane (400 ml) under stirring. This mixture was cooled to 15–18° C. 4-Methyl-5-hydroxymethyl-thiazole (50.0 g), dissolved in dichloro-methane (100 ml) was added to the above mixture in 1 hour at 15–25° C. with vigorous stirring. The reaction mixture was stirred at 25–30° C. The progress of the reaction was monitored by HPLC. The solution was decanted from the reaction mixture to separate the inorganic residue. The inorganic residue was extracted with dichloromethane (200 ml). All the dichloromethane washings were pooled and concentrated to half, which was diluted with of IPE (400 ml). The combined organic layer was washed with water, dried over Na$_2$SO$_4$. The solvent was distilled off at 40° C. under reduced pressure to get the title compound (30 g), (purity by HPLC: >99%).

What is claimed is:

1. A process for the preparation of 4-methyl-5-formyl-thiazole of the formula (I)

(I)

which comprises oxidising 4-methyl-5-hydroxymethyl thiazole of the formula (IV) to form the 4-methyl-5-formyl-thiazole of the formula (I),

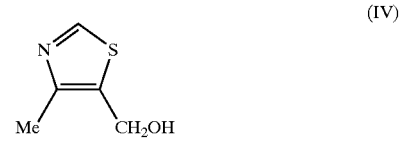

(IV)

by using an oxidizing agent selected from the group consisting of pyridinium chlorochromate, NaOCl and KBr, in the presence of a solvent.

2. The process according to claim 1, wherein the oxidizing agent is selected from the group consisting of pyridinium chlorochromate, NaOCl and KBr in presence of TEMPO or Jones reagent (CrO$_3$/H$_2$SO$_4$).

3. The process according to claim 1, wherein the solvent used is dichloromethane or ethylacetate.

4. The process according to claim 1, wherein the compound of formula (IV) is oxidized at a temperature of from −10° C. to 50° C.

5. The process according to claim 1, further comprising converting the compound of formula (I) into Cefditoren pivoxil.

6. The process according to claim 1, further comprising reducing thiazole ester of the formula (III)

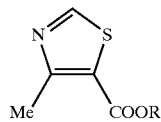 (III)

wherein R represents $(C_1-C_4)$alkyl group, using sodium borohydride, in the presence of $AlCl_3$, in a solvent, to form said 4-methyl-5-hydroxymethyl thiazole of the formula (IV).

7. The process according to claim 6, wherein the $(C_1-C_4)$ alkyl group is selected from the group consisting of methyl, ethyl, n-propyl, iso-propyl, tert-butyl.

8. The process according to claim 6, wherein the oxidizing agent is selected from the group consisting of pyridium chlorochromate, NaCOl and KBr in presence of TEMPO or Jones reagent $(CrO_3/H_2SO_4)$.

9. The process according to claim 6, wherein the solvent used in reducing the thiazole ester of the formula (III) is selected from the group consisting of monoglyme, THF and diglyme.

10. The process according to claim 6, wherein the solvent used in oxidizing the compound of the formula (IV) is dichloromethane or ethylacetate.

11. The process according to claim 6, wherein the compound of formula (IV) is oxidized at a temperature of from $-10°$ C. to $50°$ C.

12. The process according to claim 6, wherein the compound of formula (III) is reduced at a temperature of from $20°$ C. to $90°$ C.

* * * * *